United States Patent [19]

Cantatore et al.

[11] Patent Number: 4,933,451
[45] Date of Patent: Jun. 12, 1990

[54] POLYAMINES PARTIALLY SUBSTITUTED BY BIS-PIPERIDYL-TRIAZINES

[75] Inventors: Giuseppe Cantatore, Bitonto; Valerio Borzatta; Franca Masina, both of Bologna, all of Italy

[73] Assignee: Ciba-Geigy Corporation, Ardsley, N.Y.

[21] Appl. No.: 354,066

[22] Filed: May 22, 1989

[30] Foreign Application Priority Data

May 31, 1988 [IT] Italy .................. 20808 A/88

[51] Int. Cl.$^5$ .................. C07D 403/14; C08J 5/34
[52] U.S. Cl. .................. 544/198; 544/113; 544/209; 524/98; 524/100; 540/598
[58] Field of Search ............... 540/598; 544/113, 198, 544/209

[56] References Cited

U.S. PATENT DOCUMENTS 4,108,829  8/1978  Cassandrini et al. ............... 544/198
4,288,593  9/1981  Rody .................................. 544/198

FOREIGN PATENT DOCUMENTS 904401  3/1986  Belgium ............................. 544/198

OTHER PUBLICATIONS

Chem. Abst. 105, 209942q (1986).

Primary Examiner—Richard A. Schwartz
Assistant Examiner—J. Richter
Attorney, Agent, or Firm—Luther A. R. Hall

[57] ABSTRACT

The present invention relates to novel bis-piperidyl-triazine compounds with 2 or more triazine rings, to their use as light stabilizers, heat stabilizers and oxidation stabilizers for organic materials, in particular synthetic polymers, and to the organic materials thus stabilized.

10 Claims, No Drawings

POLYAMINES PARTIALLY SUBSTITUTED BY BIS-PIPERIDYL-TRIAZINES

It is known that snythetic polymers undergo a progressive change in mechanical strength and variations in colour when they are exposed to sunlight or other sources of ultraviolet light in the presence of oxygen.

To retard the photooxidative degradation of synthetic polymers, it has been proposed to use various additives having photostabilizing properties such as some derivatives of benzophenone and benzotriazole, nickel complexes, substituted benzoic acid esters, alkylidenemalonates, cyanoacrylates, aromatic oxamides and sterically hindered amines.

Some triazine derivatives of 2,2,6,6-tetramethyl-4-piperidylamine have shown a remarkable activity as light stabilizers.

In particular, U.S. Pat. Nos. 4,108,829, 4,288,593 and BE-A-904,401 describe, for example, dialkylenetriamines which contain polyalkyl-4-piperidyltriazine groups.

The present invention relates to novel bis-piperidine-triazine compounds of the general formula (I)

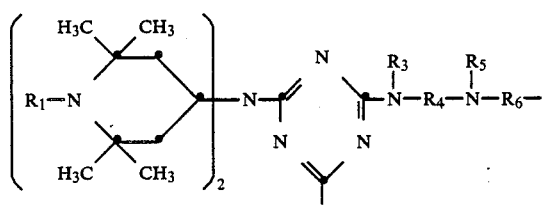

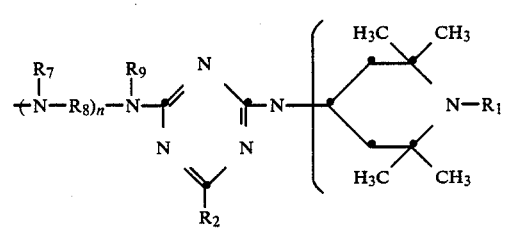

in which $R_1$ is hydrogen, $C_1$-$C_4$alkyl, O·, OH, NO, $CH_2CN$, $C_1$-$C_{18}$alkoxy, $C_5$-$C_{12}$cycloalkoxy, $C_3$-$C_6$alkenyl, $C_7$-$C_9$phenylalkyl which is unsubstituted or mono-, di- or tri-substituted on the phenyl by $C_1$-$C_4$alkyl, $C_1$-$C_8$acyl or $C_2$-$C_4$alkyl substituted by one OH in the 2-, 3- or 4-position, $R_2$ is $C_1$-$C_{18}$alkyl, phenyl which is unsubstituted or mono-, di- or tri-substituted by $C_1$-$C_4$alkyl, a group $-OR_{10}$, $-SR_{10}$ or $$-\underset{\underset{R_{11}}{|}}{N}-R_{12}$$

where $R_{10}$ is $C_1$-$C_{18}$alkyl, $C_5$-$C_{12}$cycloalkyl which is unsubstituted or mono-, di- or tri-substituted by $C_1$-$C_4$alkyl, $C_3$-$C_6$alkenyl, phenyl which is unsubstituted or mono-, di- or tri-substituted by $C_1$-$C_4$alkyl, $C_7$-$C_9$phenylalkyl which is unsubstituted or mono-, di- or tri-substituted on the phenyl by $C_1$-$C_4$alkyl, or a group of the formula (II)

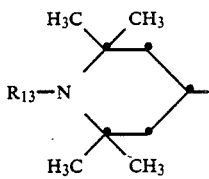

with $R_{13}$ being as defined above for $R_1$, $R_{11}$ and $R_{12}$ which are identical or different are hydrogen, $C_1$-$C_{18}$alkyl, $C_5$-$C_{12}$cycloalkyl which is unsubstituted or mono-, di- or tri-substituted by $C_1$-$C_4$alkyl, $C_3$-$C_6$alkenyl, $C_7$-$C_9$phenylalkyl which is unsubstituted or mono-, di- or tri-substituted on the phenyl by $C_1$-$C_4$alkyl, or $C_2$-$C_4$alkyl which is substituted in the 2-, 3- or 4-position by OH, by $C_1$-$C_8$alkoxy or by di($C_1$-$C_4$alkyl)amino, or a group of the formula (II), or $R_{11}$ and $R_{12}$, together with the nitrogen atom to which they are linked, form part of a 5-membered to 7-membered heterocyclic ring, $R_3$ and $R_9$ which can be identical or different are hydrogen, $C_1$-$C_{18}$alkyl, $C_5$-$C_{12}$cycloalkyl which is unsubstituted or mono-, di- or tri-substituted by $C_1$-$C_4$alkyl, $C_3$-$C_6$alkenyl, $C_7$-$C_9$phenylalkyl which is unsubstituted or mono-, di- or tri-substituted on the phenyl by $C_1$-$C_4$alkyl, $C_2$-$C_4$alkyl substituted in the 2-, 3- or 4-position by OH, or a group of the formula (II), or $R_5$ and $R_7$ are one of the groups of the formulae (IIIa)–(IIIf)

$-COR_{14}$,   $-(CH_2)_pCOOR_{15}$,   $-COR_{16}COOR_{17}$, (IIIa)          (IIIb)                (IIIc)

$$-(CH_2)_pCON\underset{\underset{R_{18}}{|}}{-}R_{19}, \quad -SO_2R_{20}, \quad -\underset{\underset{R_{21}}{|}}{C}=\underset{\underset{R_{22}}{|}}{C}-COOR_{23}$$

(IIId)          (IIIe)                (IIIf)

where $R_{14}$ is hydrogen, $C_1$-$C_{17}$alkyl, $C_5$-$C_{12}$cycloalkyl which is unsubstituted or mono-, di- or tri-substituted by $C_1$-$C_4$alkyl, $C_2$-$C_{17}$alkenyl, phenyl which is unsubstituted or mono-, di- or tri-substituted by $C_1$-$C_4$alkyl and/or an OH group, $C_7$-$C_9$phenylalkyl which is unsubstituted or mono-, di- or tri-substituted on the phenyl by $C_1$-$C_4$alkyl and/or an OH group, p is zero or an integer from 1 to 5, $R_{15}$, $R_{17}$ and $R_{23}$ which can be identical or different are $C_1$-$C_{18}$alkyl, $C_5$-$C_{12}$cycloalkyl which is unsubstituted or mono-, di- or tri-substituted by $C_1$-$C_4$alkyl, $C_3$-$C_{18}$alkenyl or a group of the formula (II), $R_{16}$ is a direct bond, $C_1$-$C_{12}$alkylene, cyclohexylene or phenylene, $R_{18}$ and $R_{19}$ which can be identical or different are as defined above for $R_{11}$ and $R_{12}$, $R_{20}$ is $C_1$14 $C_{18}$alkyl or phenyl which is unsubstituted or mono-, di- or tri-substituted by $C_1$-$C_4$alkyl, $R_{21}$ is hydrogen, $C_1$-$C_4$alkyl or phenyl, $R_{22}$ is —CN or a group —$COOR_{23}$ with $R_{23}$ being as defined above, or $R_7$ is a group of the formula (IV)

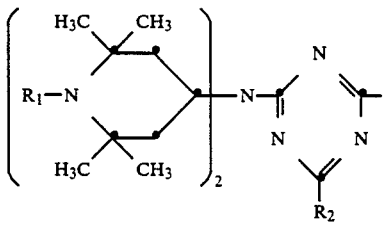

(IV)

with $R_1$ and $R_2$ being as defined above, and, if n is zero or if $R_7$ is a group of the formula (IV), $R_5$ can also be one of the groups of the formulae (Va)–(Vd)

$-R_{24}X_1$, $-(CH_2)_qCOX_1$, $-COR_{25}COX_1$, $-COOR_{26}OOCX_1$ (Va)    (Vb)      (Vc)         (Vd)

where $R_{24}$ is $C_2-C_{12}$alkylene, 2-hydroxytrimethylene or xylylene, q is an integer from 1 to 5, $R_{25}$ is as defined above for $R_{16}$, $R_{26}$ is $C_2-C_{12}$alkylene, $C_4-C_{12}$alkylene interrupted by 1, 2 or 3 oxygen atoms, cyclohexylenedimethylene, methylenedicyclohexylene, isopropylidenedicyclohexylene, phenylene xylylene or a group

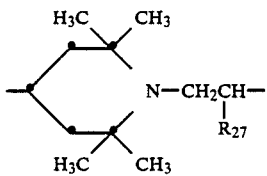

with $R_{27}$ being hydrogen, $C_1-C_4$alkyl or phenyl, and $X_1$ is a group of the formula (VI)

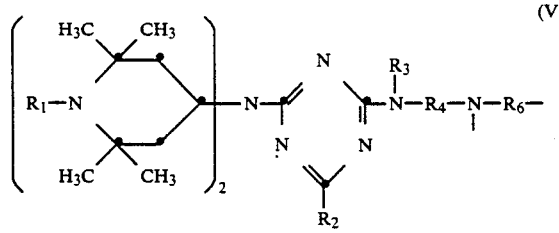
(VI)

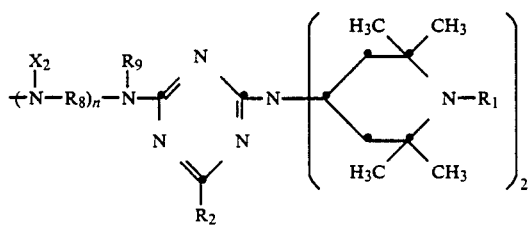

where $R_1$, $R_2$, $R_3$, $R_4$, $R_6$, $R_8$, $R_9$ and n are as defined above, and $X_2$ is a group of the formula (IV).

Representative examples of $C_1-C_4$alkyl $R_1$, $R_{13}$, $R_{21}$ and $R_{27}$ are methyl, ethyl, propyl, butyl and isobutyl. Methyl is preferred. Examples of $C_1-C_{18}$alkyl are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl tetradecyl, hexadecyl and octadecyl.

$R_3$, $R_5$, $R_7$ and $R_9$ are preferably $C_1-C_{12}$alkyl, in particular $C_1-C_4$alkyl.

Examples of OH-substituted $C_2-C_4$alkyl are 2-hydroxyethyl, 2-hydroxypropyl, 3-hydroxypropyl, 2-hydroxybutyl and 4-hydroxybutyl.

$R_1$ and $R_{13}$ are preferably 2-hydroxyethyl.

Examples of $C_2-C_4$alkyl substituted by $C_1-C_8$alkoxy, preferably $C_1-C_4$alkoxy, in particular methoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2-C_4$alkyl substituted by di($C_1-C_4$alkyl)amino, preferably dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

Representative examples of $C_1-C_{18}$alkoxy $R_1$ and $R_{13}$ are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. $C_6-C_{12}$alkoxy, in particular heptoxy or octoxy, is preferred.

Examples of $C_5-C_{12}$a cycloalkyl which is unsubstituted or substituted by $C_1-C_4$alkyl, in particular methyl, are cyclopenetyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl, Cyclohexyl is preferred.

Representative examples of $C_5-C_{12}$cycloalkoxy $R_1$ and $R_{13}$ are cyclopentoxy, cyclohexoxy, cycloheptoxy, cyclooctoxy, cyclodecyloxy and cyclododecyloxy. Cyclopentoxy and cyclohexoxy are preferred.

Examples of alkenyl having up to 18 carbon atoms are vinyl, allyl, 2-methylallyl, hexenyl, decenyl, undecenyl and oleyl. In an alkenyl group $R_1$, $R_5$, $R_7$, $R_{10}$, $R_{11}$, $R_{12}$, $R_{13}$, $R_{15}$, $R_{17}$, $R_{18}$, $R_{19}$ and $R_{23}$, the carbon atom in the α-position is conveniently a primary carbon atom. $R_1$ and $R_{13}$ are preferably allyl.

Phenyl $R_2$, $R_{10}$ and $R_{20}$ substituted by $C_1-C_4$alkyl is in particular methylphenyl, dimethylphenyl, trimethylphenyl, t-butylphenyl or di-t-butylphenyl.

Representative examples of phenyl $R_{14}$ substituted by $C_1-C_4$alkyl and/or OH are 3,5-di-t-butyl-4-hydroxyphenyl, methylphenyl, dimethylphenyl, trimethylphenyl, t-butylphenyl and di-t-butylphenyl.

Representative examples of $C_7-C_9$phenylalkyl $R_1$, $R_5$, $R_7$, $R_{10}$, $R_{11}$, $R_{12}$, $R_{13}$, $R_{18}$ and $R_{19}$, which is unsubstituted or substituted by $C_1-C_4$alkyl, are benzyl, methylbenzyl, dimethylbenzyl, t-butylbenzyl and 2-phenylethyl. Benzyl is preferred.

$C_7-C_9$phenylalkyl $R_{14}$, which is unsubstituted or substituted on the phenyl group by $C_1-C_4$alkyl and/or OH, is in particular 2-(3,5-di-t-butyl-4-hydroxyphenyl)ethyl, benzyl, methylbenzyl, dimethylbenzyl, t-butylbenzyl or 2-phenylethyl.

Representative examples of $C_1-C_8$acyl $R_1$ and $R_{13}$, which can be aliphatic or aromatic, are formyl, acetyl, propionyl, butyryl, valeryl, hexanoyl, octanoyl, benzoyl, acryloyl and crotonyl. $C_1-C_8$alkanoyl, $C_3-C_8$alkenoyl and benzoyl are preferred. Acetyl is especially preferred.

Examples of alkylene having up to 12 carbon atoms are methylene, ethylene, propylene, trimethylene, tetramethylene, pentamethylene, 2,2-dimethyltrimethylene, hexamethylene, trimethylhexamethylene, decamethylene and dodecamethylene. Alkylene having up to 8 carbon atoms, especially up to 6 carbon atoms, is preferred.

$R_4$, $R_6$ and $R_8$ are in particular $C_2$–$C_3$alkylene.

Examples of $C_4$–$C_{12}$alkylene interrupted by 1, 2 or 3 oxygen atoms are 3oxapentane-1,5-diyl, 3,6-dioxaoctane-1,8-diyl and 3,6,9-trioxaundecane-1,11-diyl.

If $R_{11}$ and $R_{12}$ or $R_{18}$ and $R_{19}$, together with the nitrogen atom to which they are linked, form a 5-membered to 7-membered heterocyclic radical, the said heterocyclic group preferably contains a further heteroatom, for example nitrogen or oxygen. Examples are pyrrolidyl, piperidyl, morpholinyl, N-methylpiperazinyl and hexahydroazepinyl.

Those compounds of the formula (I) are preferred in which $R_2$ is $C_1$–$C_{12}$alkyl, phenyl, a group —$OR_{10}$, —$SR_{10}$ or

where $R_{10}$ is $C_1$–$C_{12}$alkyl, $C_5$–$C_8$cycloalkyl which is unsubstituted or mono-, di- or tri-substituted by $C_1$–$C_4$alkyl, allyl, phenyl, benzyl or a group of the formula (II), $R_{11}$ and $R_{12}$ which can be identical or different are hydrogen, $C_1$–$C_{12}$alkyl, $C_5$–$C_8$cycloalkyl which is unsubstituted or mono-, di- or tri-substituted by $C_1$–$C_4$alkyl, allyl, benzyl, $C_2$–$C_3$alkyl substituted in the 2- or 3-position by OH, by $C_1$–$C_4$akoxy or by di($C_1$–$C_4$alkyl)amino, or a group of the formula (II), or the group

is 1-pyrrolidyl, 1-piperidyl, 4-morpholinyl or 1-hexahydroazepinyl, $R_3$ and $R_9$ which can be identical or different are hydrogen, $C_1$–$C_{12}$alkyl, $C_5$–$C_8$cycloalkyl which is unsubstituted or mono-, di- or tri-substituted by $C_1$–$C_4$alkyl, or a group of the formula (II), $R_4$, $R_6$ and $R_8$ which can be identical or different are $C_2$–$C_{10}$alkylene, n is zero or 1, $R_5$ and $R_7$ which can be identical or different are hydrogen, $C_1$–$C_{12}$alkyl, $C_5$–$C_8$cycloalkyl which is unsubstituted or mono-, di- or tri-substituted by $C_1$–$C_4$alkyl, allyl, benzyl, $C_2$–$C_3$alkyl substituted in the 2- or 3-position by OH, a group of the formula (II) or one of the groups of the formulae (IIIa)–(IIIf) in which $R_{14}$ is hydrogen, $C_1$–$C_{17}$alkyl, $C_5$–$C_8$cycloalkyl which is unsubstituted or mono-, di- or tri-substituted by $C_1$–$C_4$alkyl, $C_2$–$C_{17}$alkenyl, phenyl which is unsubstituted or mono-, di- or tri-substituted by $C_1$–$C_4$alkyl and/or an OH group, $C_7$–$C_8$phenylalkyl which is unsubstituted or mono-, di- or tri-substituted on the phenyl by $C_1$–$C_4$alkyl and/or an OH group, p is zero or an integer from 1 to 3, $R_{15}$, $R_{17}$ and $R_{23}$ which can be identical or different are $C_1$–$C_{18}$alkyl, $C_5$–$C_8$cycloalkyl which is unsubstituted or mono-, di- or tri-substituted by $C_1$–$C_4$alkyl, $C_3$–$C_{18}$alkenyl or a group of the formula (II), $R_{16}$ is a direct bond or $C_1$–$C_{10}$alkylene, $R_{18}$ and $R_{19}$ which can be identical or different are $C_1$–$C_{12}$alkyl, cyclohexyl, allyl, benzyl or a group of the formula (II) or the group

is 1-pyrrolidyl, 1-piperidyl, 4-morpholinyl or 1-hexahydroazepinyl, $R_{20}$ is $C_1$–$C_{12}$alkyl, phenyl or tolyl, $R_{21}$ is hydrogen or $C_1$–$C_4$alkyl, $R_{22}$ is —CN or a group —$COOR_{23}$ with $R_{23}$ as defined above, or $R_7$ is a group of the formula (IV) and $R_5$ can also be one of the groups of the formulae (Va)–(Vd) in which $R_{24}$ is $C_2$–$C_{10}$alkylene, 2-hydroxytrimethylene or xylylene, q is an integer from 1 to 3, $R_{25}$ is a direct bond or $C_1$–$C_{10}$alkylene, $R_{26}$ is $C_2$–$C_{10}$alkylene, $C_4$–$C_8$alkylene interrupted by 1, 2 or 3 oxygen atoms, cyclohexylene dimethylene, isopropylidenedicyclohexylene or a group

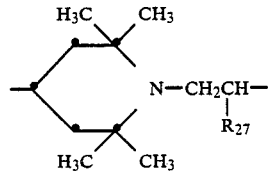

with $R_{27}$ being hydrogen or methyl, and $X_1$ is a group of the formula (VI).

Those compounds of the formula (I) are particularly preferred in which $R_2$ is $C_1$–$C_4$alkyl, phenyl, a group —$OR_{10}$, —$SR_{10}$, —$SR_{10}$ or

where $R_{10}$ is $C_1$–$C_8$alkyl, cyclohexyl which is unsubstituted or mono-, di- or tri-substituted by $C_1$–$C_4$alkyl, allyl, phenyl, benzyl or a group of the formula (II), $R_{11}$ and $R_{12}$ which can be identical or different are hydrogen, $C_1$–$C_{12}$alkyl, cyclohexyl which is unsubstituted or mono-, di- or tri-substituted by $C_1$–$C_4$alkyl, allyl, benzyl, $C_2$–$C_3$alkyl which is substituted in the 2- or 3-position by OH, by methoxy, by ethoxy, by dimethylamino or by diethylamino, or a group of the formula (II), or the group

is 4-morpholinyl, $R_3$ and $R_9$ which can be identical or different are hydrogen, $C_1$–$C_8$alkyl, cyclohexyl which is unsubstituted or mono-, di- or tri-substituted by $C_1$–$C_4$alkyl, or a group of the formula (II), $R_4$, $R_6$ and $R_8$ which can be identical or different are $C_2$–$C_8$alkylene, n is zero or 1, $R_5$ and $R_7$ which can be identical or different are hydrogen, $C_1$–$C_8$alkyl, cyclohexyl which is unsubstituted or mono-, di- or tri-substituted by $C_1$–$C_4$alkyl, allyl, benzyl, 2-hydroxyethyl or one of the groups of the formula (IIIa)–(IIIf) in which $R_{14}$ is $C_1$–$C_{17}$alkyl, cyclohexyl which is unsubstituted or mono-, di- or tri-substituted by $C_1$–$C_4$alkyl, $C_2$–$C_{10}$alkenyl, phenyl, 3,5-di-t-butyl-4-hydroxyphenyl, benzyl or 2-(3,5-di-t-butyl-4-hydroxyphenyl)ethyl, p is zero or 1, $R_{15}$, $R_{17}$ and $R_{23}$ which can be identical or different are $C_1$–$C_{18}$alkyl, cyclohexyl which is unsubstituted or mono-, di- or tri-substituted by $C_1$–$C_4$alkyl, allyl, oleyl or a group of the formula (II), $R_{16}$ is a direct bond or $C_1$–$C_8$alkylene, $R_{18}$ and $R_{19}$ which can be identical or different are $C_1$–$C_8$alkyl, cyclohexyl, allyl, benzyl or a group of the formula (II), or the group

is 4-morpholinyl, $R_{20}$ is $C_1-C_8$alkyl, phenyl or tolyl, $R_{21}$ is hydrogen or methyl and $R_{22}$ is —CN or a group —COOR$_{23}$ with $R_{23}$ being as defined above, or $R_7$ is a group of the formula (IV) and $R_5$ can also be one of the groups of the formulae (Va)–(Vd) in which $R_{24}$ is $C_2-C_8$alkylene, 2-hydroxytrimethylene or xylylene, q is 1 or 2, $R_{25}$ is a direct bond or $C_1-C_8$alkylene, $R_{26}$ is $C_2-C_8$alkylene, $C_4-C_6$alkylene interrupted by 1 or 2 oxygen atoms, cyclohexylenedimethylene, isopropylidenedicyclohexylene or a group

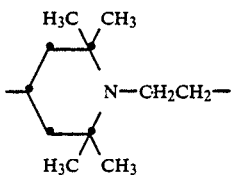

and $X_1$ is a group of the formula (VI).

Those compounds of the formula (I) are of special interest in which $R_2$ is a group

where $R_{11}$ is a group of the formula (II) and $R_{12}$ is hydrogen, $C_1-C_8$alkyl, cyclohexyl, $C_1-C_3$alkyl substituted in the 2- or 3-position by OH, by methoxy or by ethoxy, or a group of the formula (II), $R_3$ and $R_9$ which can be identical or different are hydrogen, $C_1-C_4$alkyl, cyclohexyl or a group of the formula (II), $R_4$, $R_6$ and $R_8$ which can be identical or different are $C_2-C_6$alkylene, n is zero or 1, $R_5$ and $R_7$ which can be identical or different are hydrogen, $C_1-C_4$alkyl, allyl, benzyl or one of the groups of the formulae (IIIa), (IIIb), (IIIc) or (IIIf) in which $R_{14}$ is $C_1-C_{17}$alkyl, cyclohexyl, t-butylcyclohexyl, phenyl, 3,5-di-t-butyl-4-hydroxyphenyl or 2-(3,5-di-t-butyl-4-hydroxyphenyl)ethyl and p is zero, $R_{15}$ and $R_{17}$ which can be identical or different are $C_1-C_{18}$alkyl, cyclohexyl, t-butylcyclohexyl or a group of the formula (II), $R_{16}$ is a direct bond, $R_{21}$ is hydrogen or methyl, $R_{22}$ is —CN or a group —COOR$_{23}$ where $R_{23}$ is $C_1-C_8$alkyl, or $R_7$ is a group of the formula (IV) and $R_5$ can also be one of the groups of the formula (Vc) or (Vd) in which $R_{25}$ is a direct bond or $C_1-C_8$alkylene, $R_{26}$ is $C_4-C_8$alkylene, 3-oxapentane-1,5-diyl, cyclohexylenedimethylene or isopropylidenedicyclohexylene and $X_1$ is a group of the formula (VI).

Those compounds of the formula (I) are of particular interest in which $R_1$ is hydrogen or methyl, $R_2$ is a group

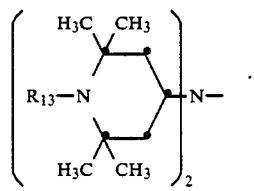

with $R_{13}$ being hydrogen or mehtyl, $R_3$ and $R_9$ which can be identical or different are hydrogen or methyl, $R_4$, $R_6$ and $R_8$ which can be identical or different are —(CH$_2$)$_{2-3}$—, n is zero or 1, $R_5$ and $R_7$ which can be identical or different are hydrogen, methyl or one of the groups of the formula (IIIa), (IIIb) or (IIIf) in which $R_{14}$ is $C_1-C_{15}$alkyl and p is zero, $R_{15}$ is $C_1-C_{16}$alkyl, $R_{21}$ is hydrogen, $R_{22}$ is —CN and $R_{23}$ is $C_1-C_4$alkyl, or $R_7$ is a group of the formula (IV) and $R_5$ can also be one of the groups of the formula (Vc) or (Vd) in which $R_{25}$ is —(CH$_2$)$_r$— with r being an integer from 1 to 8, $R_{26}$ is $C_4-C_6$alkylene and $X_1$ is a group of the formula (IV).

Also of interest are those compounds of formula (I) wherein $R_1$ and $R_{13}$ independently of one another are hydrogen, $C_1-C_4$alkyl, OH, $C_6-C_{12}$alkoxy, $C_5-C_8$cycloalkoxy, allyl, benzyl, acetyl or 2-hydroxyethyl, in particular hydrogen or methyl.

$R_2$ as the group

is particularly preferred.

Those compounds of the formula (I) are also of interest in which $R_3$ and $R_9$ independently of one another are hydrogen, $C_1-C_4$alkyl or a group of the formula (II), $R_5$ and $R_7$ independently of one another are hydrogen, $C_1-C_4$alkyl or a group of the formula (IIIa), (IIIb) or (IIIf), $R_7$ is in addition a group of the formula (IV) and $R_5$ is in addition a group of the formula (Vc) or (Vd).

Preferred compounds of formula (I) are those of Examples 1, 6, 9, 11, 15 and 17.

The compounds of the formula (I) can be prepared for example by processes known per se, e.g. by reacting a chlorotriazine of the formula (VII)

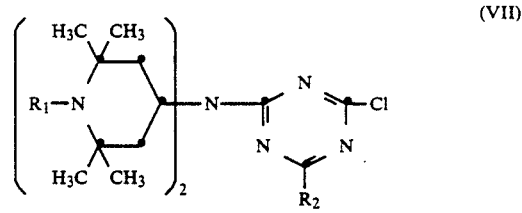

with $R_1$ and $R_2$ being as defined above, with a polyamine of the formula (VIII)

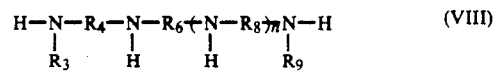

with $R_3$, $R_4$, $R_6$, $R_8$, $R_9$ and n being as defined above, by operating as described for example in U.S. Pat. No. 4,108,829, with a molar ratio of compound of the formula (VII): compound of the formula (VIII) being equal to e.g. 2:1 if n is zero, and e.g. 2:1 or 3:1 if n is 1.

Compounds of the formula (I) are preferably obtained in this way in which $R_5$ is hydrogen and $R_7$ is hydrogen or a group of the formula (IV); from these compounds, the corresponding compounds with $R_5$ and $R_7$ other than H can be obtained successively e.g. by reaction with suitable alkylating or acylating reagents.

If $R_5$ and $R_7$ are $C_1-C_{18}$alkyl, $C_5-C_{12}$cycloalkyl, $C_7-C_9$phenylalkyl or a group of the formula (II), the compounds of the formula (I) can be obtained directly, for example by reacting a chlorotriazine of the formula (VII) with a polyamine of the formula (IX)

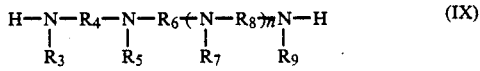

in which $R_3$, $R_4$, $R_6$, $R_8$, $R_9$ and n are as defined before and $R_5$ and $R_7$ are as defined above.

If $R_5$ and $R_7$ are methyl, the compounds of the formula (I) are preferably prepared by reacting the corresponding unsubstituted compounds with formaldehyde and formic acid (Eschweiler-Clarke reaction) or with formaldehyde and hydrogen in the presence of a hydrogenation catalyst such as e.g. palladium or platinum.

In these reactions, the piperidine

groups can also be methylated and, under suitable conditions, also the melamine

groups which may be present.

The reactions of the chlorotriazines of the formula (VII) with the polyamines of the formula (VIII) or (IX) are preferably carried out in an aromatic chyrocarbon solvent, for example toluene, xylene, ethylbenzene or trimethylbenzene, operating at a temperature from e.g. $-20°$ C. to 200° C., preferably from $-10°$ C. to 180° C. The successive substitution reactions are preferably carried out by directly using the reaction mixture obtained in the first stage, but it is also possible to separate the intermediate compounds with $R_5$ and possibly $R_7=H$, and using them in the successive alkylation or acylation reactions followed ultimately by purification using, if appropriate, a solvent other than that employed in the first stage.

The hydrohalic acid eliminated in the various reactions is preferably neutralized with an inorganic base such as e.g. sodium or potassium hydroxide or carbonate, in a quantity at least equivalent to the acid eliminated.

As mentioned at the outset, the compounds of the formula (I) are highly effective in improving the light stability, heat stability and oxidation stability of organic materials, in particular synthetic polymers. The very high stabilizing activity of the compounds of the invention against oxidation is particularly surprising. The invention therefore also relates to a composition containing an organic material, which is susceptible to thermal, oxidative or light-induced degradation, and at least one compound of the formula (I).

Examples of organic materials which can be stabilized are:

1. Polymers of monoolefins and diolefins, for example polypropylene, polyisobutylene, polybutene-1, polymethylpentene-1, polyisoprene or polybutadience, as well as polymers of cycloolefins, for instance of cyclopentene or norbornene, polyethylene (which optionally can be crosslinked), for example high density polyethylene (HDPE), low density polyethylene (LDPE) and linear low densitypolyethylene (LLDPE).

2. Mixtures of the polymers mentioned under (1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefines and diolefines with each other or with other vinyl monomers, such as, for example, ethylene/propylene, linear low density polyethylene (LLDPE) and its mixtures with low density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene; as well as mixtures of such copolymers and their mixtures with polymers mentioned in (1) above, for example polypropylene/ethylene-propylene-copolymers, LDPE/EVA, LDPE/EAA, LLDPE/EVA and LLDPE/EAA.

3a. Hydrocarbon resins (for example $C_5-C_9$) and hydrogenated modifications thereof (for example tackyfiers).

4. Polystyrene, poly-(p-methylstyrene), poly-($\alpha$-methylstyrene).

5. Copolymers of styrene or $\alpha$-methylstyrene with diences or acrylic derivatives, such as, for example, styrene/butadiene, styrene/acrylonitrile, styrene/alkyl methacrylate, styrene/maleic anhydride, styrene/butadiene/ethyl acrylate, styrene/acrylonitrile/methyl acrylate; mixtures of high impact strength from styrene copolymers and another polymer, such as, for example, from apolyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or $\alpha$-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthate or polyallylmelamine; as well as their copolymers with olefins mentioned in (1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, poolyamide 12, aromatic polyamides obtained by condensation of m-xylene diamine and adipic acid; polyamides prepared from hexamethylenediamine and isophthalic or/and terephthalic acid and optionally an elastomer as modifier, for example poly-2,4,4,-trimethylhexamethylene terephthalamide or poly-m-phenylene isophthalamide. Further copolymers of the aforementioned polyamides with polyolefins, olefin copolymers, ionomers or chemically bonded or grafted elastomers; or with polyethers, such as for instance, with polyethylene glycols, polypropylene glycols or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly-[2,2,-(4-hydroxyphenyl)propane] terephthalate and polyhydroxybenzoates as well as block-copolyether-esters derived from polyethers having hydroxyl end groups.

18. Polycarbonates and polyester-carbonates.

19. Polysulfones, polyether-sulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyester-crylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymer-homologous manner, such as cellulose acetates, cellulose propionates and cellulose butyrates, or the cellulose ethers, such as methylcellulose; rosins and their derivatives.

27. Mixtures of polymers as mentioned above, for example PP/EPDM, Polyamide 6/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

Compounds of the formula (I) are particularly suitable for improving the light stability, heat stability and oxidation stability of polyolefins, especially polyethylene and polypropylene.

The compounds of the formula (I) can be used in mixtures with organic materials in various proportions depending on the nature of the material to be stabilized, on the end use and on the presence of other additives.

In general, it is advantageous to use, for example, 0.01 to 5% by weight of the compounds of the formula (I) relative to the weight of the material to be stabilized, preferably 0.05 to 1%.

The compounds of the formula (I) can be incorporated in the polymeric materials by various processes, such as e.g. dry mixing in the form of powder, or wet mixing in the form of solutions or suspensions or also in the form of a masterbatch; in such operations, the polymer can be used in the form of powder, granules, solutions, suspensions or in the form of latices.

The polymers stabilized with the products of the formula (I) can be used e.g. for the production of mouldings, films, tapes, monofilaments, surface coatings and the like.

If desired, other conventional additives for synthetic polymers, such as e.g. antioxidants, UV absorbers, nickel stabilizers, pigments, fillers, plasticizers, antistatic agents, flameproofing agents, lubricating agents, corrosion inhibitors and metal deactivators, can be added to the mixtures of the compounds of the formula (I) with the organic materials. Particular examples of additives which can be used in a mixture with the compounds of the formula (I) are:

1. Antioxidants 1.1. Alkylated monophenls, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4methylphenyl] terephthalate.

1.5. Benzylcompounds, for example 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanuate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl)isocyanurate.

1.6. Acylaminophenols, for example lauric acid 4-hydroxyanilide, stearic acid 4-hydroxyanilide, 2,4-bis(octylmercapto)-6-(3,5-di-tert-butyl-4-hydroxyanilino)-s-triazine, octyl N-(3,5-di-tert-butyl-4-hydroxyphenyl)-carbamate.

1.7. Esters of β-(3,5-di-tert-butyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.8. Esters of β-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.9. Esters of β-(3,5-dicyclohexyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.10. Amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)-trimethylene-diamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis(α,α-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example, 4-tert-butylphenyl salicylate, phenyl salicylate, octylphenyl salicylate, dibenzoylresorcinol, bis(4-tert-butylbenzoyl)-resorcinol, benzoylresorcinol, 2,4-di-tert-butylphenyl 3,5-di-tert-butyl-4-hyroxybenzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzyl-phosphonic acid monoalkyl esters, e.g. of the methyl or ethyl ester, nickel complexes of ketoximes, e.g. of 2-hydroxy-4-methyl-phenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensation product of 1-(2-hydroxyethyl)-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butanetetracarboxylate, 1,1'-(1,2-ethanediyl)bis(3,3,5,5-tetramethylpiperazinone).

2.7. Oxalic acid diamides, for example 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-disubstituted oxanilides and mixtures of o-and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

3. Metal deactivators, for example N,N'-diphenyloxalic acid diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalodihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tertbutylphenyl) pentaerythritol diphosphite, tristearyl sorbitol triphosphite, tetrakis(2,4-di-tert-butylphenyl) 4,4'-biphenylene diphosphonite, 3,9-bis(2,4-di-tert-butylphenoxy)-2,4,8,10-tetraoxa-3,9-diphosphaspiro[5.5]undecane.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example copper salts in combination with iodides and/or phosphorus compounds and salts of divalent manganese.

7. Basic co-stabilisers, for example, melamine, polyvinylpyrrolidone, dicyandiamide, triallyl cyanurate, urea derivates, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

In order to illustrate the present invention more clearly, several examples of the preparation and the use of compounds of the formula (I) are described below; these examples are given by way of illustration only and do not imply any restriction.

EXAMPLE 1

Preparation of

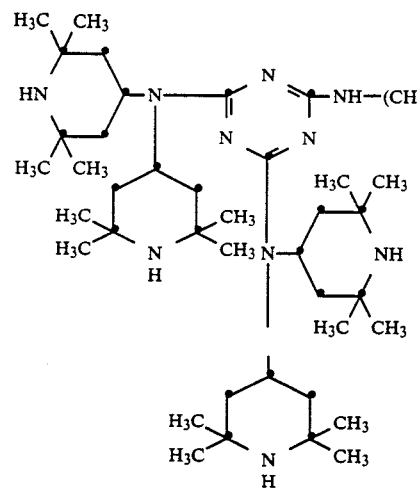
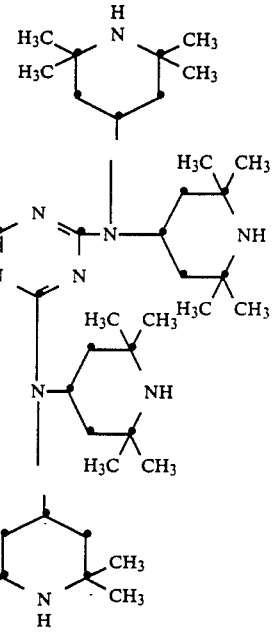

70.25 g (0.1 mol) of 2-chloro-4,6-bis[N',N-bis(2,2,6,6-tetramethyl-4-piperidyl)-amino]-1,3,5-triazine and 5.16 g (0.05 mol) of diethylenetriamine in 300 ml of xylene are heated for 2 hours under reflux.

After the addition of 6.0 g (0.15 mol) of finely powdered sodium hydroxide, the mixture is heated for 16 hours under reflux, the water of reaction being simultaneously separated off azeotropically.

The mixture is cooled to ambient temperature and filtered. The organic solution is evaporated in vacuo (24 mbar), a product of melting point 194°–197° C. being obtained.

Analysis for $C_{82}H_{155}N_{21}$:
Calculated: C=68.62%; H=10.88%; N=20.49%;
Found: C=68.24%; H=10.82%; N=20.29%.
EXAMPLE 2-4
Proceeding analogously to Example 1 and using the proper reagents in appropriate molar ratios, the products of the formula:
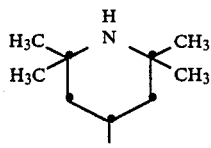
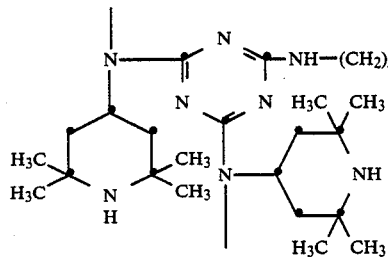
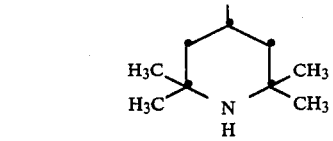
are obtained.
| Example | n | R | s | t | u | m.p. °C. |
|---|---|---|---|---|---|---|
| 2 | 0 | — | 3 | 3 | — | 177–181 |
| 3 | 1 | H | 3 | 2 | 3 | 162–166 |
-continued
| Example | n | R | s | t | u | m.p. °C. |
|---|---|---|---|---|---|---|
| 4 | 1 | 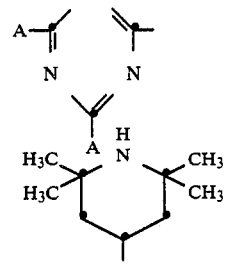 | 3 | 2 | 3 | 205–209 |
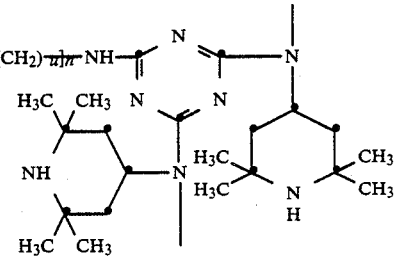
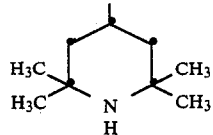
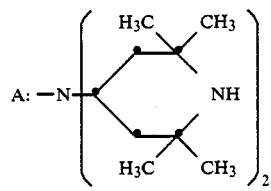
EXAMPLE 5
Preparation of
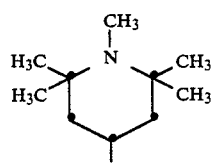
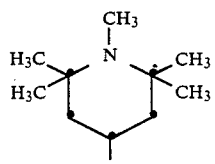
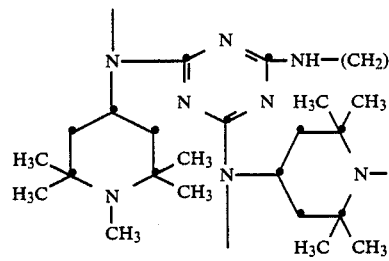
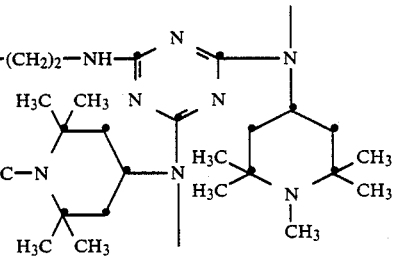

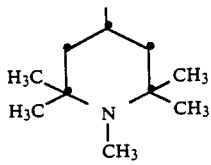 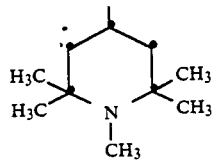

-continued

A solution consisting of 8.74 g (0.19 mole) of formic acid and 5.71 g (0.19 mole) of paraformaldehyde, previously dissolved in 10 ml of water containing 0.07 g of sodium hydroxide, is slowly added to a solution, heated to 110° C., of 28.70 g (0.02 mole) of the product from Example 1 in 70 ml of xylene, the added water in the water of reaction being removed azeotropically.

After the end of the addition, the mixture is heated for 1 hour at 110° C. It is cooled to 80° C., and a solution of 2.9 g (0.07 mole) of sodium hydroxide in 15 ml of water is added. The mixture is heated for 1 hour under reflux and cooled to 80° C., and the aqueous phase is separated off.

After washing with twice 50 ml of water, the organic solution is evaporated in vacuo (24 mbar), a product of melting point 242°–247° C. being obtained.

Analysis for $C_{91}H_{173}N_{21}$:
Calculated: C=70.00%; H=11.17%; N=18.94%;
Found: C=69.84%; H=11.08%; N=18.63%.

EXAMPLES 6-8

Proceeding analogously to Example 5 using the respective intermediates and reagents in appropriate molar ratios, the products of the formula

| Example | n | R | s | t | u | m.p. °C. |
|---|---|---|---|---|---|---|
| 6 | 0 | — | 3 | 3 | — | 226–230 |
| 7 | 1 | —CH₃ | 3 | 2 | 3 | 206–210 |
| 8 | 1 | 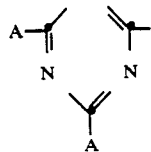 | 3 | 2 | 3 | 240–245 |

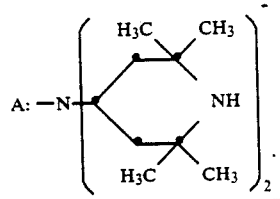

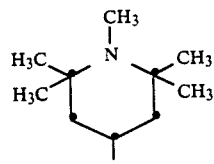 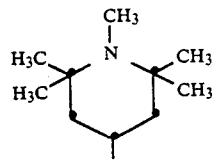

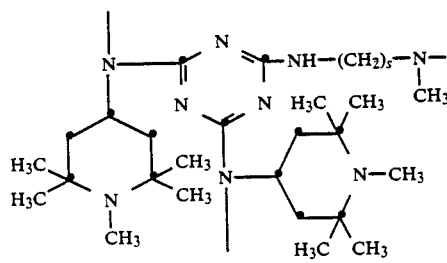 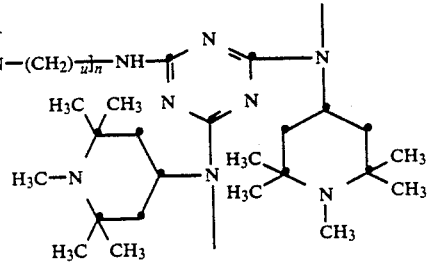

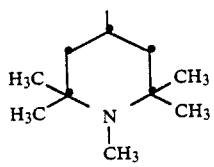 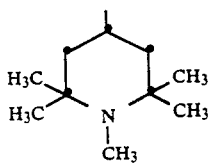

are obtained.

EXAMPLE 9

Preparation of

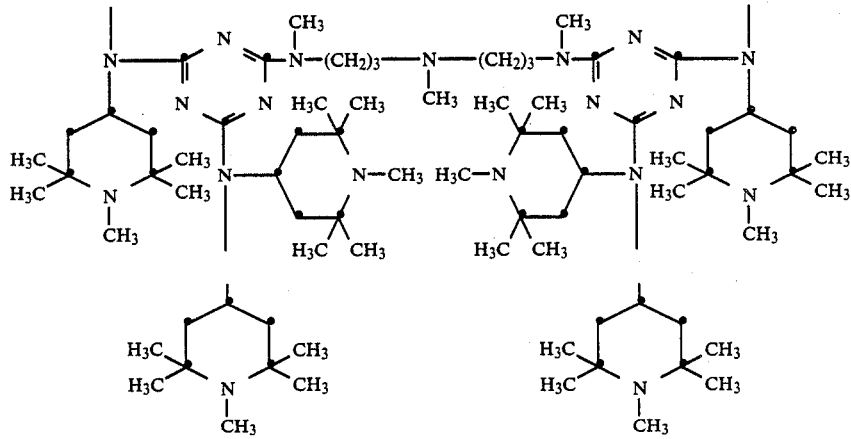

16.1 g (0.011 mole) of the product from Example 2 are dissolved in an aqueous solution of 16.5 g (0.36 mole) of formic acid in 100 ml of water. 10.8 g (0.36 mole) of paraformaldehyde are added to the aqueous solution thus obtained, which is then heated for 12 hours under reflux.

After cooling, a solution of 24 g (0.6 mole) of sodium hydroxide in 50 ml of water is added, and the mixture is heated for 1 hour at 70°–80° C., cooled and filtered. The solid separated out is washed repeatedly with water and dried in an oven at 130° C. in vacuo (2 mbar).

This gives a product of melting point 216°–220° C.

Analysis for $C_{95}H_{181}N_{21}$;
Calculated: C=70.54%; H=11.28%; N=18.18%;
Found: C=70.16%; H=11.21%, N=18.21%.

EXAMPLE 10

Preparation of

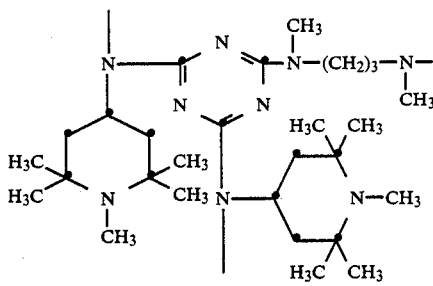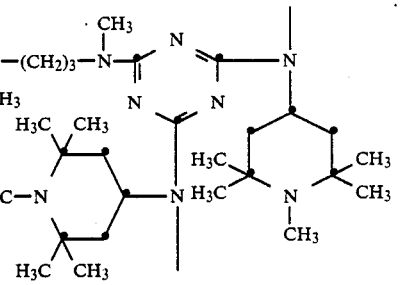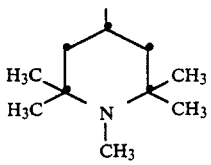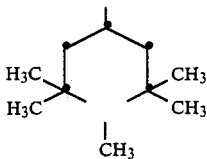

Proceeding analogously to Example 9, 16.5 g (0.011 mole) of the product from Example 3 are reacted with 18.4 g (0.4 mole) of formic acid in 100 ml of water and 12 g (0.4 mole) of paraformaldehyde, a product of melting point 201°–206° C. being obtained.

Analysis for $C_{98}H_{188}N_{22}$:
Calculated: C=70.29%; H=11.31%; N=18.40%;
Found: C=69.98%; H=11.25%; N=18.17%.

EXAMPLE 11

Preparation of

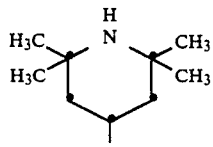
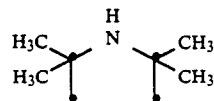
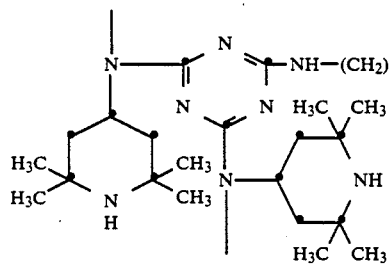
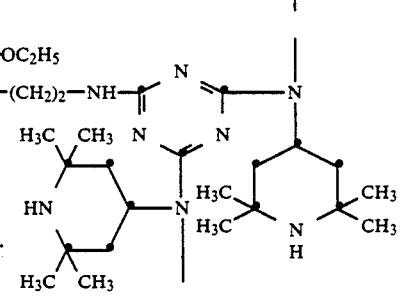
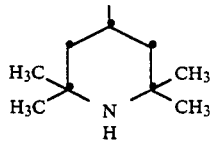
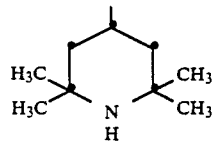

1.30 g (0.012 mole) of ethyl chloroformate are added slowly to a solution, cooled to 0°–5° C., of 17.22 g (0.012 mole) of the product from Example 1 in 90 ml of xylene. After the end of the addition, the solution is stirred for 2 hours at a temperature indicated above, and an aqueous solution of 0.56 g (0.014 mole) of sodium hydroxide in 10 ml of water is then added. The mixture is then stirred for 1 hour at ambient temperature, 40 ml of water are added and the organic phase is separated off. After washing with water, the organic solution is evaporated in vacuo (24 mbar), a product of melting point 187°–191° C. being obtained.

Analysis for $C_{85}H_{159}N_{21}O_2$;
Calculated: C=67.73%; H=10.63%; N=19.51%;
Found: C=67.12%; H=10.55%; N=19.32%.

EXAMPLES 12–14

Proceeding analogously to Example 11 and using the respective intermediates and reagents in appropriate molar ratios, the products of the formula

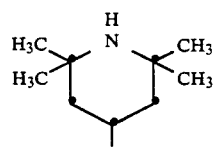
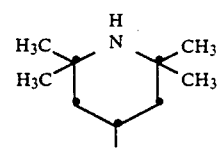
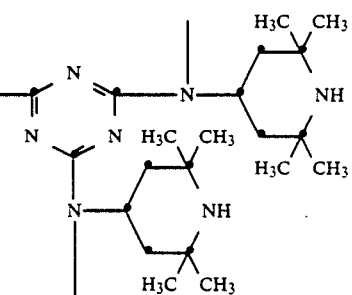
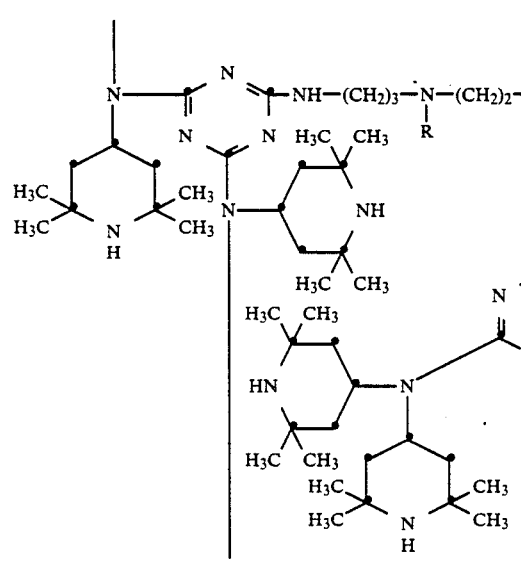

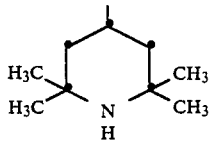
are obtained.
| Example | R | m.p. °C. |
|---|---|---|
| 12 | —COOC$_{14}$H$_{29}$ | 168–172 |
| 13 | —COOC$_4$H$_9$ | 191–195 |
| 14 | —COOC$_2$H$_5$ | 197–201 |
EXAMPLE 15
Preparation of
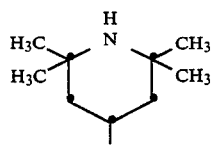
Proceeding analogously to Example 11, 28.70 g (0.02 mole) of the product from Example 1 are reacted with 2.15 g (0.01 mole) of 1,4-butanediol bis-chloroformate in 100 ml of xylene, a product of melting point 219°–224° C. being obtained.
Analysis for $C_{170}H_{316}N_{42}O_4$:
Calculated: C=67.78%; H=10.57%; N=19.53%;
Found: C=67.13%; H=10.50%; N=19.60%.
EXAMPLE 16
Preparation of
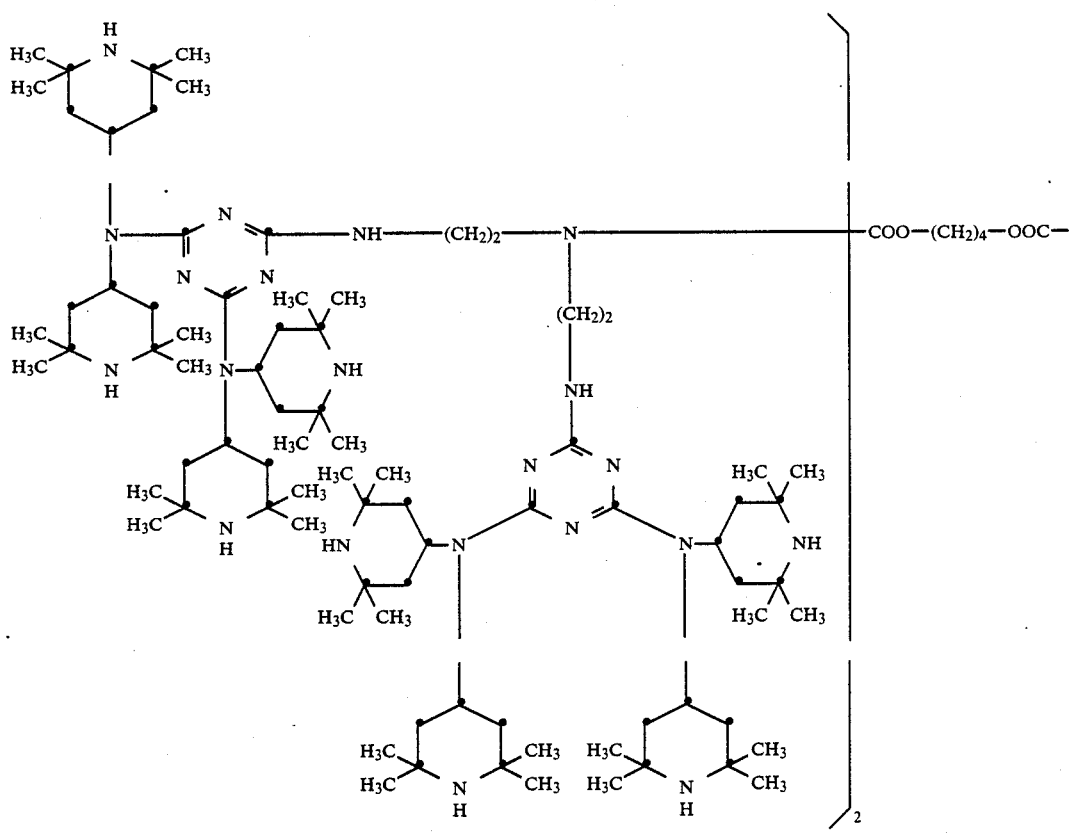

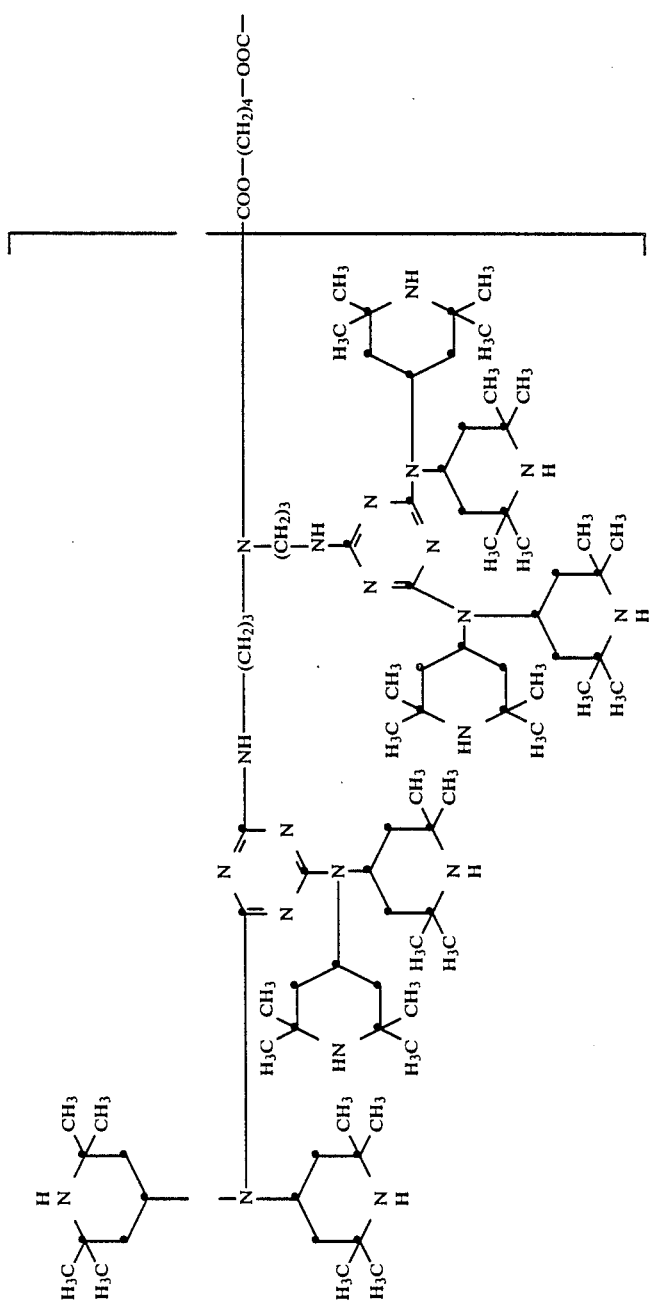

Proceeding analogously to Example 11, 35.12 g (0.024 mole) of the product from Example 2 are reacted with 2.58 g (0.012 mole) of 1,4-butanediol bis-chloroformate in 150 ml of xylene, a product of melting point 200°–204° C. being obtained.

Analysis for $C_{174}H_{324}N_{42}O_4$:

Calculated: C=68.10%; H=10.64%; N=19.17%;
Found: C=67.74%; H=10.65%; N=18.93%.

EXAMPLE 17

Preparation of

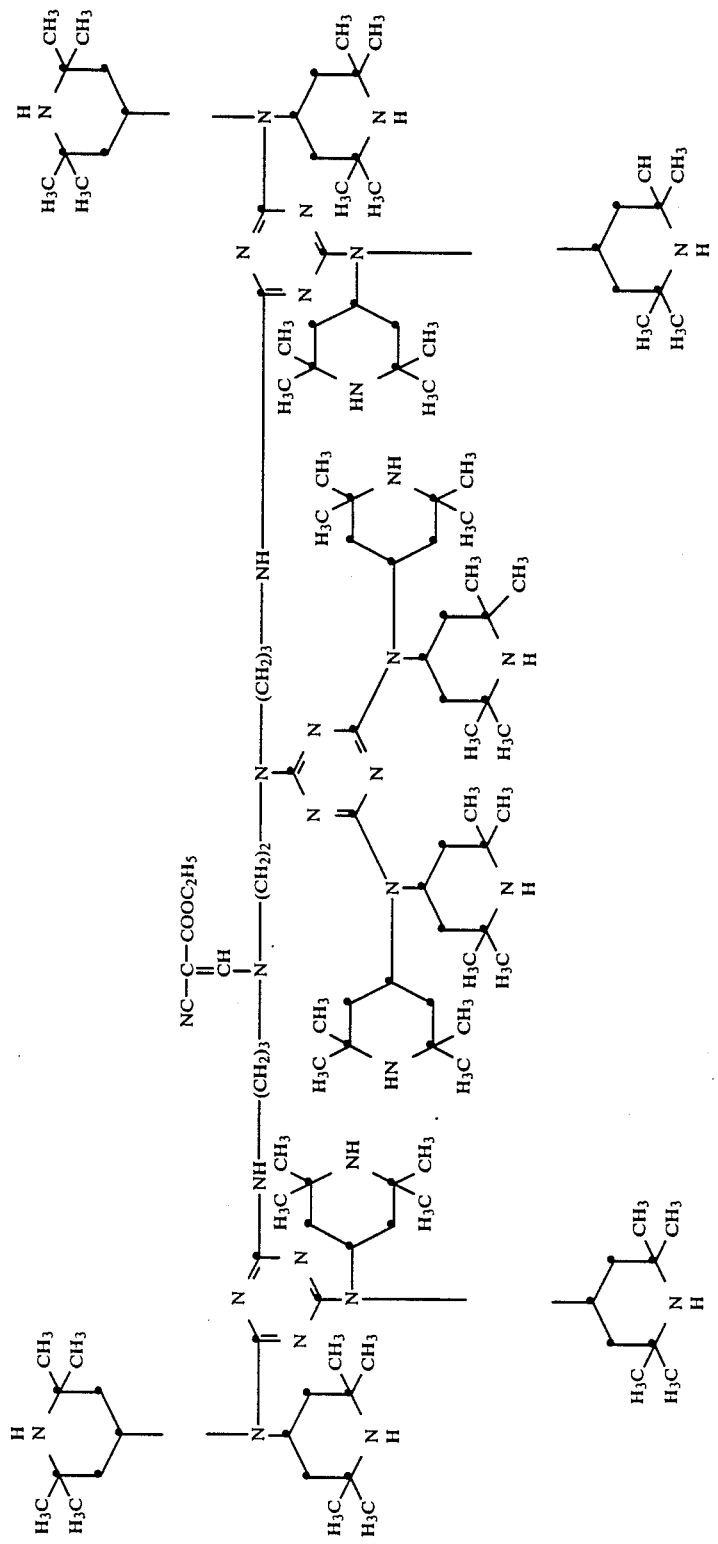

A solution of 1.36 g (0.008 mole) of ethyl (ethoxymethylene)-cyanoacetate in 10 ml of xylene is added slowly to a solution, heated to 35°–40° C., of 17.38 g (0.008 mole) of the product from Example 4 in 70 ml of xylene.

After the end of the addition, the mixture is heated for 5 hours at 60° C. and for a further 5 hours at 80° C.

The solution is washed with water and evaporated in vacuo (24 mbar), a product of melting point 179°–183° C. being obtained.

Analysis for $C_{131}H_{240}N_{32}O_2 \times 5H_2O$;
Calculated: C=65.93%; H=10.56%; N=18.78%;
Found: C=66.01%; H=10.48%; N=18.34%.

EXAMPLE 18

Preparation of

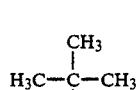

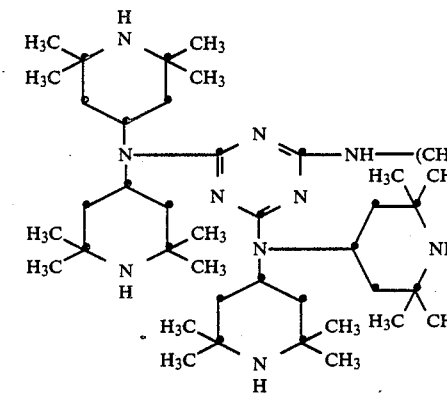

21.95 g (0.015 mole) of the product from Example 2 are dissolved in 140 ml of dichloroethane, and a solution of 1.93 g (0.016 mole) of pivaloyl chloride in 15 ml of dichloroethane is added to the solution thus obtained, cooled to 0° C. After the end of the addition, the solution is stirred for 2 hours at ambient temperature and, after cooling to 0° C., a solution of 0.64 g (0.016 mole) of sodium hydroxide in 7 ml of water is added.

The mixture is then stirred at ambient temperature for 1 hour and diluted with 20 ml of water. The organic phase is separated off, washed with water, dried over sodium sulphate, filtered and evaporated in vacuo (24 mbar), a product of melting point 169°–173° C. being obtained.

Elemental analysis for $C_{89}H_{167}N_{21}O$:
Calculated: C=69.08%; H=10.88%; N=19.01%;
Found: C=68.90%; H=10.80%; N=18.79%.

EXAMPLE 19

Antioxidant action in polypropylene plaques 1 g of each of the compounds indicated in Table 1 and 1 g of calcium stearate are mixed in a slow mixer with 1,000 g of polypropylene powder of melt index=2 g/10 minutes (measured at 230° C. and 2.16 kg).

The mixtures are extruded twice at 200°–220° C. to give polymer granules which are then converted into plaques of 1 mm thickness (mould according to DIN 54,451) by compression-moulding for 3 minutes at 220° C.

The plaques obtained are exposed in a forced-circulation air oven maintained at a temperature of 135° C.

The specimens are periodically checked by bending through 180°, in order to determine the time (in hours) required for the onset of embrittlement.

Plaques prepared under the same conditions as indicated above, but without the addition of stabilizers, are exposed for comparison.

The results obtained are shown in Table 1.

TABLE 1

| Stabilizer | Time to embrittlement (hours) |
|---|---|
| without stabilizer | 250 |
| compound from Example 1 | 1,630 |
| compound from Example 2 | 1,480 |
| compound from Example 3 | 1,580 |
| compound from Example 4 | 1,500 |
| compound from Example 9 | 2,040 |
| compound from Example 10 | 1,780 |
| compound from Example 11 | 1,660 |
| compound from Example 15 | 1,420 |
| compound from Example 17 | 1,750 |

EXAMPLE 20

Light-stabilizing action in polypropylene tapes 1 g of each of the compounds indicated in Table 2, 0.5 g of tris-(2,4-di-t-butylphenyl) phosphite, 0.5 g of pentaerythritol tetrakis-3-(3,5-di-t-butyl-4-hydroxyphenyl)-propionate and 1 g of calcium stearate are mixed in a slow mixer with 1,000 g of propylene powder of melt index=2 g/10 minutes (measured at 230° C. and 2.16 kg).

The mixtures are extruded at 200°–220° C. to give polymer granules which are then converted into stretched tapes of 50 μm thickness and 2.5 mm width, using a pilot-type apparatus (Leonard-Sumirago (VA) Italy) under the following conditions:
extruder temperature: 210°–230° C.
head temperature: 240°–260° C.
stretch ratio: 1:6

The tapes thus prepared are exposed, mounted on a white card, in a model 65 WR Weather-O-Meter (ASTM G 26-77) at a black panel temperature of 63° C.

The residual tenacity is measured on samples, taken after various times of exposure to light, by means of a constant-speed tensometer; the exposure time (in hours) needed to halve the initial tenacity is then calculated (T50).

Tapes prepared under the same conditions as indicated above, but without the addition of stabilizer, are exposed for comparison.

The results obtained are shown in Table 2:

TABLE 2

| Stabilizer | T50 (hours) |
|---|---|
| without stabilizer | 500 |

TABLE 2-continued

| Stabilizer | T50 (hours) |
| --- | --- |
| compound from Example 1 | 2,850 |
| compound from Example 2 | 2,860 |
| compound from Example 3 | 2,680 |
| compound from Example 4 | 2,860 |
| compound from Example 5 | 2,700 |
| compound from Example 6 | 3,100 |
| compound from Example 8 | 2,850 |
| compound from Example 11 | 3,390 |
| compound from Example 15 | 2,700 |
| compound from Example 17 | 2,740 |
| compound from Example 18 | 2,920 |

EXAMPLE 21

Light-stabilizing action in polypropylene fibres 2.5 g of each of the products indicated in Table 2, 0.5 g of tris-(2,4-di-t-butylphenyl) phosphite, 0.5 g of calcium monoethyl 3,5-di-t-butyl-4-hydroxybenzylphosphonate, 1 g of calcium stearate and 2.5 g of titanium dioxide (KRONOS RN 57) are mixed in a slow mixer with 1,000 g of polypropylene powder of melt index=12 g/10 minutes (measured at 230° C. and 2.16 kg).

The mixtures are extruded at 200°–220° C. to give polymer granules which are then converted into fibres, using a pilot-type apparatus (Leonard-Sumirago (VA), Italy) and operating under the following conditions:
 extruder temperature: 200°–230° C.
 head temperature: 255°–260° C.
 stretch ratio: 1:3.5
 denier: 11 dtex per filament The fibres thus produced are exposed, mounted on a white card, in a 65 WR model Weather-O-Meter (ASTM G 26-77) at a black panel temperature of 63° C.

The residual tenacity is measured on samples, taken after various times of exposure to light, by means of a constant-speed tensometer; the exposure time in hours, needed to halve the initial tenacity is then calculated (T50).

Fibres prepared under the same conditions as indicated above, but without the addition of compounds according to the invention, are exposed for comparison.

The results obtained are shown in Table 3.

TABLE 3

| Stabilizer | T50 (hours) |
| --- | --- |
| without stabilizer | 150 |
| compound from Example 6 | 1,450 |
| compound from Example 11 | 1,600 |
| compound from Example 15 | 1,460 |

What is claimed is:
1. A compound of the formula (I)

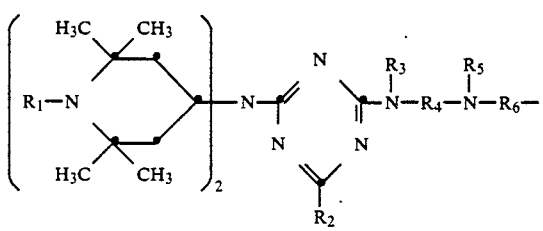

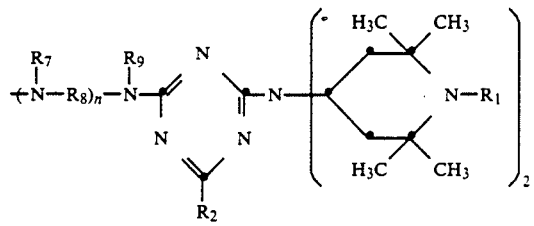

in which $R_1$ is hydrogen, $C_1$–$C_4$alkyl, O·, OH, NO, $CH_2CN$, $C_1$–$C_{18}$alkoxy, $C_5$–$C_{12}$cycloalkoxy, $C_3$–$C_6$alkenyl, phenyl-$C_1$–$C_3$-alkyl which is unsubstituted or mono-, di- or tri-substituted on the phenyl by $C_1$–$C_4$alkyl, $C_1$–$C_8$acyl or $C_2$–$C_4$alkyl substituted by one OH in the 2-, 3- or 4-position, $R_2$ is $C_1$–$C_{18}$alkyl, phenyl which is unsubstituted or mono-, di- or tri-substituted by $C_1$–$C_4$alkyl, a group —$OR_{10}$, —$SR_{10}$ or

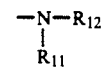

where $R_{10}$ is $C_1$–$C_{18}$alkyl, $C_5$–$C_{12}$cycloalkyl which is unsubstituted or mono-, di- or tri-substituted by $C_1$–$C_4$alkyl, $C_3$–$C_6$alkenyl, phenyl which is unsubstituted or mono, di- or tri-substituted by $C_1$–$C_4$alkyl, phenyl-$C_1$–$C_3$-alkyl which is unsubstituted or mono-, di- or tri-substituted on the phenyl by $C_1$–$C_4$alkyl, or a group of the formula (II)

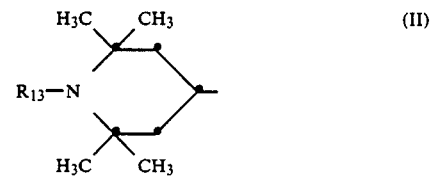

with $R_{13}$ being as defined above for $R_1$; $R_{11}$ and $R_{12}$ which are identical or different are hydrogen, $C_1$–$C_{18}$alkyl, $C_5$–$C_{12}$cycloalkyl which is unsubstituted or mono, di- or tri-substituted by $C_1$–$C_4$alkyl, $C_3$–$C_6$alkenyl, phenyl-$C_1$–$C_3$-alkyl which is unsubstituted or mono, di or tri-substituted on the phenyl by $C_1$–$C_4$alkyl, or $C_2$–$C_4$alkyl which is substituted in the 2-, 3- or 4-position by OH, by $C_1$–$C_8$alkoxy or by di($C_1$–$C_4$alkyl)amino, or a group of the formula (II), or $R_{11}$ and $R_{12}$, together with the nitrogen atom to which they are linked, form part of a 5-membered to 7-membered heterocyclic ring; $R_3$ and $R_9$ which are identical or different are hydrogen, $C_1$–$C_{18}$alkyl, $C_5$–$C_{12}$cycloalkyl which is unsubstituted or mono-, di- or tri-substituted by $C_1$–$C_4$alkyl, or a group of formula (II); $R_4$, $R_6$ and $R_8$ which are identical or different are $C_2$–$C_{12}$alkylene, n is 0 or 1, $R_5$ and $R_7$ which are identical or different are hydrogen, $C_1$–$C_{18}$alkyl, $C_5$–$C_{12}$cycloalkyl which is unsubstituted or mono-, di- or tri-substituted by $C_1$–$C_4$alkyl, $C_3$–$C_6$alkenyl, phenyl-$C_1$–$C_3$-alkyl which is unsubstituted or mono-, di- or tri-substituted on the phenyl by $C_1$–$C_4$alkyl, $C_2$–$C_4$alkyl substituted in the 2-, 3- or 4-position by OH, or a group of the formula (II), or $R_5$ and $R_7$ are one of the groups of the formulae (IIIa)–(IIIf)

—COR₁₄,  —(CH₂)ₚCOOR₁₅,  —COR₁₆COOR₁₇, (IIIa)      (IIIb)           (IIIc)

—(CH₂)ₚCON—R₁₉,  —SO₂R₂₀,  —C=C—COOR₂₃
         |                    |  |
         R₁₈                  R₂₁ R₂₂

(IIId)         (IIIe)      (IIIf)

where $R_{14}$ is hydrogen, $C_1$–$C_{17}$alkyl, $C_5$–$C_{12}$cycloalkyl which is unsubstituted or mono-, di- or tri-substituted by $C_1$–$C_4$alkyl, $C_2$–$C_{17}$alkenyl, phenyl which is unsubstituted or mono, di- or tri-substituted by $C_1$–$C_4$alkyl or an OH group, 3,5-di-tert-butyl-4-hydroxyphenyl, which is unsubstituted or mono-, di- or tri-substituted on the phenyl by $C_1$–$C_4$alkyl or an OH group, 2-(3,5-di-tert-butyl-4-hydroxyphenyl)ethyl, p is zero or an integer from 1 to 5, $R_{15}$, $R_{17}$ and $R_{23}$ which are identical or different are $C_1$–$C_{18}$alkyl, $C_5$–$C_{12}$cycloalkyl which is unsubstituted or mono-, di- or tri-substituted by $C_1$–$C_4$alkyl, $C_3$–$C_{18}$alkenyl or a group of the formula (II), $R_{16}$ is a direct bond, $C_1$–$C_{12}$alkylene, cyclohexylene or phenylene, $R_{18}$ and $R_{19}$ which are identical or different are as defined above for $R_{11}$ and $R_{12}$; $R_{20}$ is $C_1$–$C_{18}$alkyl or phenyl which is unsubstituted or mono-, di- or tri-substituted by $C_1$–$C_4$alkyl, $R_{21}$ is hydrogen, $C_1$–$C_4$alkyl or phenyl, $R_{22}$ is —CN or a group —COOR₂₃ with $R_{23}$ being as defined above, or $R_7$ is a group of the formula (IV)

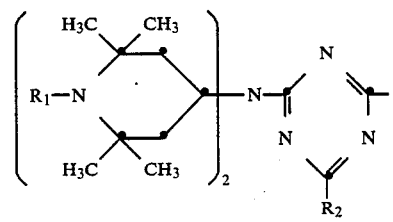

(IV)

with $R_1$ and $R_2$ being as defined above, and, if n is zero or if $R_7$ is a group of the formula (IV), $R_5$ is also one of the groups of the formulae (Va)–(Vd)

—R₂₄X₁,  —(CH₂)ᵩCOX₁,  —COR₂₅COX₁,  —COOR₂₆OOCX₁

(Va)      (Vb)         (Vc)            (Vd)

where $R_{24}$ is $C_2$–$C_{12}$alkylene, 2-hydroxytrimethylene or xylylene, q is an integer from 1 to 5, $R_{25}$ is as defined above for $R_{16}$, $R_{26}$ is $C_2$–$C_{12}$alkylene, $C_4$–$C_{12}$alkylene interrupted by 1, 2 or 3 oxygen atoms, cyclohexylenedimethylene, methylenedicyclohexylene, isopropylidenedicyclohexylene, phenylene, xylylene or a group

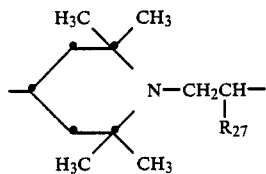

with $R_{27}$ being hydrogen, $C_1$–$C_4$alkyl or phenyl, and $X_1$ is a group of the formula (VI)

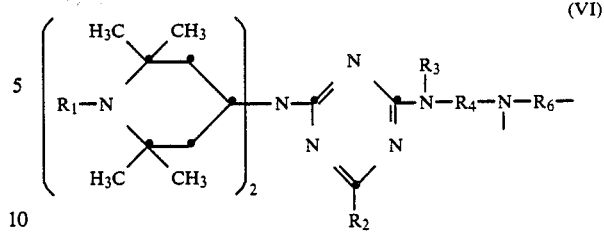

(VI)

where $R_1$, $R_2$, $R_3$, $R_4$, $R_6$, $R_8$, $R_9$ and n are as defined above, and $X_2$ is a group of the formula (IV).

2. A compound of the formula (I) according to claim 1, in which $R_2$ is $C_1$–$C_{12}$alkyl, phenyl, a group —OR₁₀, —SR₁₀ or

—N—R₁₂
 |
 R₁₁ where $R_{10}$ is $C_1$–$C_{12}$alkyl, $C_5$–$C_8$cycloalkyl which is unsubstituted or mono-, di- or tri-substituted by $C_1$–$C_4$alkyl, allyl, phenyl, benzyl or a group of the formula (II); $R_{11}$ and $R_{12}$ which are identical or different are hydrogen, $C_1$–$C_{12}$alkyl, $C_5$–$C_8$cycloalkyl which is unsubstituted or mono-, di- or tri-substituted by $C_1$–$C_4$alkyl, allyl, benzyl, $C_2$–$C_3$alkyl substituted in the 2- or 3-position by OH, by $C_1$–$C_4$alkoxy or by di($C_1$–$C_4$alkyl)amino, or a group of the formula (II), or the group

—N—R₁₂
 |
 R₁₁ is 1-pyrrolidyl, 1-piperidyl, 4-morpholinyl or 1-hexahydroazepinyl, $R_3$ and $R_9$ which are identical or different are hydrogen, $C_1$–$C_{12}$alkyl, $C_5$–$C_8$cycloalkyl which is unsubstituted or mono-, di- or tri-substituted by $C_1$–$C_4$alkyl, or a group of the formula (II); $R_4$, $R_6$ and $R_8$ which are identical or different are $C_2$–$C_{10}$alkylene, n is zero or 1, $R_5$ and $R_7$ which are identical or different are hydrogen, $C_1$–$C_{12}$alkyl, $C_5$–$C_8$cycloalkyl which is unsubstituted or mono-, di- or tri-substituted by $C_1$–$C_4$alkyl, allyl, benzyl, $C_2$–$C_3$alkyl substituted in the 2- or 3-position by OH, a group of the formula (II) or one of the groups of the formulae (IIIa)–(IIIf) in which $R_{14}$ is hydrogen, $C_1$–$C_{17}$alkyl, $C_5$–$C_8$cycloalkyl which is unsubstituted or mono-, di- or tri-substituted by $C_1$–$C_4$alkyl, $C_2$–$C_{17}$alkenyl, phenyl which is unsubstituted or mono-, di- or tri-substituted by $C_1$–$C_4$alkyl or an OH group, 3-5-di tert-butyl-4-hydroxyphenyl, $C_7$–$C_8$phenylalkyl which is unsubstituted or mono-, di- or tri-substituted on the phenyl by $C_1$–$C_4$alkyl or an OH group, 2-(3,5-di-tert-butyl-4-hydroxyphenyl)ethyl, p is zero or an integer from 1 to 3, $R_{15}$, $R_{17}$ and $R_{23}$ which are identical or different are $C_1$–$C_{18}$alkyl, $C_5$–$C_8$cycloalkyl which is unsubstituted or mono-, di- or tri-substituted by $C_1$-$C_4$alkyl, $C_3$-$C_{18}$alkenyl or a group of the formula (II), $R_{16}$ is a direct bond or $C_1$-$C_{10}$alkylene, $R_{18}$ and $R_{19}$ which are identical or different are $C_1$-$C_{12}$alkyl, cyclohexyl, allyl, benzyl or a group of the formula (II), or the group

is 1-pyrrolidyl, 1-piperidyl, 4-morpholinyl or 1-hexahydroazepinyl, $R_{20}$ is $C_1$-$C_{12}$alkyl, phenyl or tolyl, $R_{21}$ is hydrogen or $C_1$-$C_4$alkyl and $R_{22}$ is —CN or a group —COOR$_{23}$ with $R_{23}$ being as defined above, or $R_7$ is a group of the formula (IV) and $R_5$ is also one of the groups of the formulae (Va)–(Vd) in which $R_{24}$ is $C_2$-$C_{10}$alkylene, 2-hydroxytrimethylene or xylylene, q is an integer from 1 to 3, $R_{25}$ is a direct bond or $C_1$-$C_{10}$alkylene, $R_{26}$ is $C_2$-$C_{10}$alkylene, $C_4$-$C_8$alkylene interrupted by 1, 2 or 3 oxygen atoms, cyclohexylenedimethylene, isopropylidenedicyclohexylene or a group

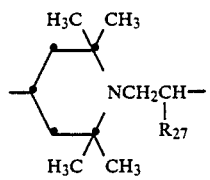

with $R_{27}$ being hydrogen or methyl, and $X_1$ is a group of the formula (VI).

3. A compound of the formula (I) according to claim 1, in which $R_2$ is $C_1$-$C_4$alkyl, phenyl, a group —OR$_{10}$, —SR$_{10}$ or

where $R_{10}$ is $C_1$-$C_8$alkyl, cyclohexyl which is unsubstituted or mono-, di- or tri-substituted by $C_1$-$C_4$alkyl, allyl, phenyl, benzyl or a group of the formula (II), $R_{11}$ and $R_{12}$ which are identical or different are hydrogen, $C_1$-$C_{12}$alkyl, cyclohexyl which is unsubstituted or mono-, di- or tri-substituted by $C_1$-$C_4$alkyl, allyl, benzyl, $C_2$-$C_3$alkyl which is substituted in the 2- or 3-position by OH or by methoxy, by ethoxy, by dimethylamino or by diethylamino, or a group of the formula (II), or the group

is 4-morpholinyl, $R_3$ and $R_9$ which are identical or different are hydrogen, $C_1$-$C_8$alkyl, cyclohexyl which is unsubstituted or mono-, di- or tri-substituted by $C_1$-$C_4$alkyl, or a group of the formula (II); $R_4$, $R_6$ and $R_8$ which are identical or different are $C_2$-$C_8$alkylene, n is zero or 1, $R_5$ and $R_7$ which are identical or different are hydrogen, $C_1$-$C_8$alkyl, cyclohexyl which is unsubstituted or mono-, di- or tri-substituted by $C_1$-$C_4$alkyl, allyl, benzyl, 2-hydroxyethyl or one of the groups of the formulae (IIIa)–(IIIf) in which $R_{14}$ is $C_1$-$C_{17}$alkyl, cyclohexyl which is unsubstituted or mono-, di- or tri-substituted by $C_1$-$C_4$alkyl, $C_2$-$C_{10}$alkenyl, phenyl, 3,5-di-t-butyl-4-hydroxyphenyl, benzyl or 2-(3,5-di-t-butyl-4-hydroxyphenyl)ethyl, p is zero or 1, $R_{15}$, $R_{17}$ and $R_{23}$ which are identical or different are $C_1$-$C_{18}$alkyl, cyclohexyl which is unsubstituted or mono-, di- or tri-substituted by $C_1$-$C_4$alkyl, allyl, oleyl or a group of the formula (II), $R_{16}$ is a direct bond or $C_1$-$C_8$akylene, $R_{18}$ and $R_{19}$ which are identical or different are $C_1$-$C_8$alkyl, cyclohexyl, allyl, benzyl or a group of the formula (II), or the group

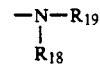

is 4-morpholinyl, $R_{20}$ is $C_1$-$C_8$alkyl, phenyl or tolyl, $R_{21}$ is hydrogen or methyl and $R_{22}$ is —CN or a group —COOR$_{23}$ with $R_{23}$ being as defined above, or $R_7$ is a group of the formula (IV) and $R_5$ is also one of the groups of the formulae (Va)–(Vd) in which $R_{24}$ is $C_2$-$C_8$alkylene, 2-hydroxytrimethylene or xylylene, q is 1 or 2, $R_{25}$ is a direct bond or $C_1$-$C_8$alkylene, $R_{26}$ is $C_2$-$C_8$alkylene, $C_4$-$C_6$alkylene interrupted by 1 or 2 oxygen atoms, cyclohexylenedimethylene, isopropylidenedicyclohexylene or a group

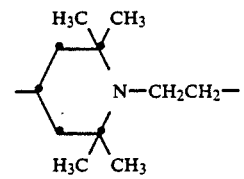

and $X_1$ is a group of the formula (VI).

4. A compound of the formula (I) according to claim 1, in which $R_2$ is a group

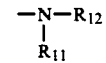

where $R_{11}$ is a group of the formula (II) and $R_{12}$ is hydrogen, $C_1$-$C_8$alkyl, cyclohexyl, $C_2$-$C_3$alkyl substituted in the 2- or 3-position by OH, by methoxy or by ethoxy, or a group of the formula (II), $R_3$ and $R_9$ which are identical or different are hydrogen, $C_1$-$C_4$alkyl, cyclohexyl or a group of the formula (II); $R_4$, $R_6$ and $R_8$ which are identicala or different are $C_2$-$C_6$alkylene, n is zero or 1, $R_5$ and $R_7$ which are identical or different are hydrogen, $C_1$-$C_4$alkyl, allyl, benzyl or one of the groups of the formulae (IIIa), (IIIb), (IIIc) or (IIIf) in which $R_{14}$ is $C_1$-$C_{17}$alkyl, cyclohexyl, t-butylcyclohexyl, phenyl, 3,5-di-t-butyl-4-hydroxyphenyl or 2-(3,5-di-t-butyl-4-hydroxyphenyl)ethyl and p is zero, $R_{15}$ and $R_{17}$ which are identical or different are $C_1$-$C_{18}$alkyl, cyclohexyl, t-butylcyclohexyl or a group of the formula (II), $R_{16}$ is a direct bond, $R_{21}$ is hydrogen or methyl, $R_{22}$ is —CN or a group —COOR$_{23}$ where $R_{23}$ is $C_1$-$C_8$alkyl, or $R_7$ is a group of the formula (IV) and $R_5$ is also one of the groups of the formula (Vc) or (Vd) in which $R_{25}$ is a direct bond or $C_1$-$C_8$alkylene, $R_{26}$ is $C_4$-$C_8$alkylene, 3-oxapentane-1,5-diyl, cyclohexylenedimethylene or isopropylidenedicyclohexylene and $X_1$ is a group of the formula (VI).

5. A compound of the formula (I) according to claim 1 in which $R_1$ is hydrogen or methyl, $R_2$ is a group

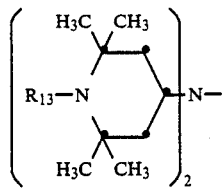

with $R_{13}$ being hydrogen or methyl, $R_3$ and $R_9$ which are identical or different are hydrogen or methyl, $R_4$, $R_6$ and $R_8$ which are identical or different are —$(CH_2)_{2-3}$—, n is zero or 1, $R_5$ and $R_7$ which are identical or different are hydrogen, methyl or one of the groups of the formula (IIIa), (IIIb) or (IIIf) in which $R_{14}$ is $C_1$-$C_{15}$alkyl and p is zero, $R_{15}$ is $C_1$-$C_{16}$alkyl, $R_{21}$ is hydrogen, $R_{22}$ is —CN and $R_{23}$ is $C_1$-$C_4$alkyl, or $R_7$ is a group of the formula (IV) and $R_5$ is also one of the groups of the formula (Vc) or (Vd) in which $R_{25}$ is —$(CH_2)_r$— with r being an integer from 1 to 8, $R_{26}$ is $C_4$-$C_6$alkylene and $X_1$ is a group of the formula (VI).

6. A compound of the formula (I) according to claim 1, in which $R_1$ and $R_{13}$ independently of one another are hydrogen, $C_1$-$C_4$alkyl, OH, $C_6$-$C_{12}$alkoxy, $C_5$-$C_8$cycloalkoxy, allyl, benzyl, acetyl or 2-hydroxyethyl.

7. A compound of the formula (I) according to claim 1, in which $R_1$ and $R_{13}$ independently of one another are hydrogen or methyl.

8. A compound of the formula (I) according to claim 1, in which $R_2$ is a group

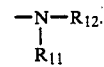

9. A compound of the formula (I) according to claim 1, in which $R_3$ and $R_9$ independently of one another are hydrogen, $C_1$-$C_4$alkyl or a group of the formula (II), $R_5$ and $R_7$ independently of one another are hydrogen, $C_1$-$C_4$alkyl or a group of the formula (IIIa), (IIIb) or (IIIf), $R_7$ is in addition a group of the formula (IV) and $R_5$ is in addition a group of the formula (Vc) or (Vd).

10. The compounds

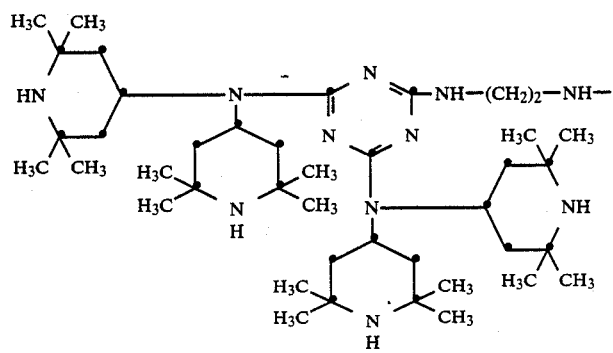
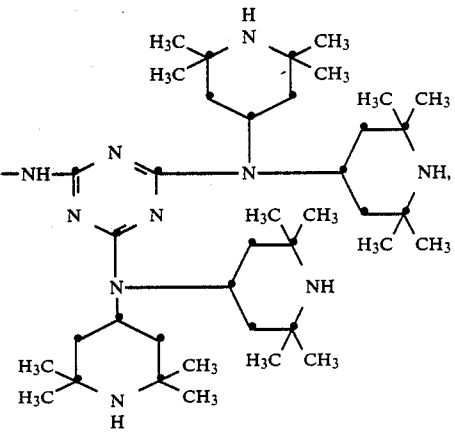
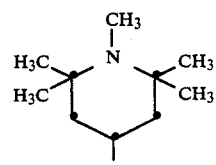
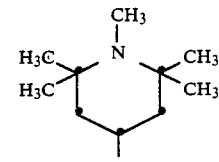
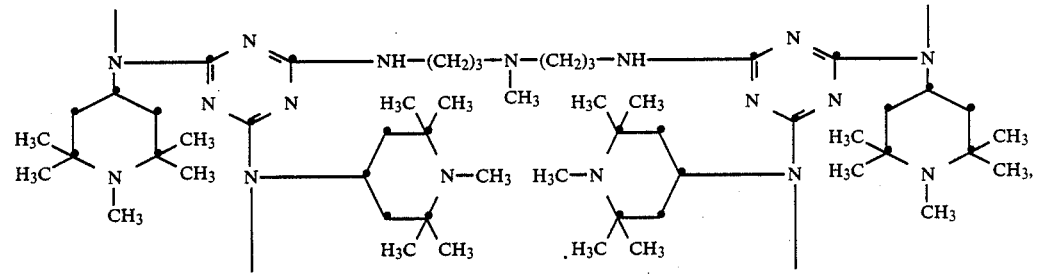
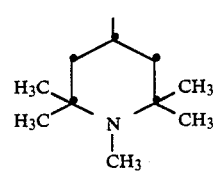
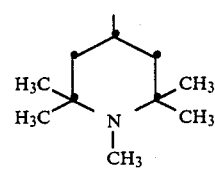

-continued
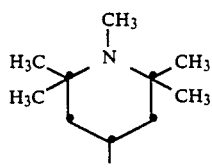
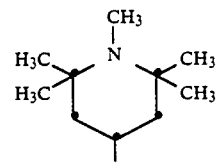
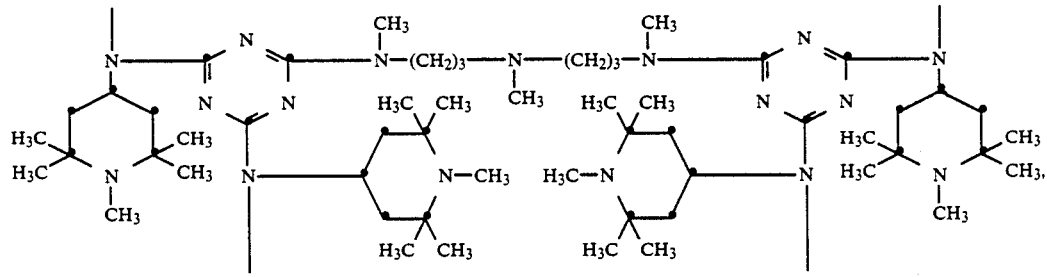
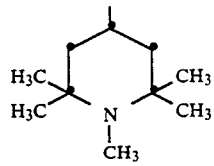
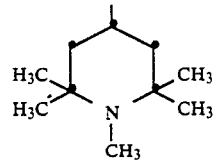
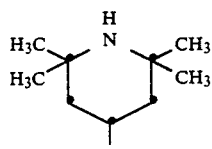
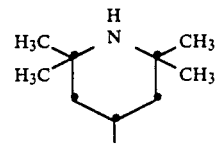
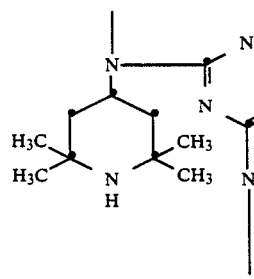
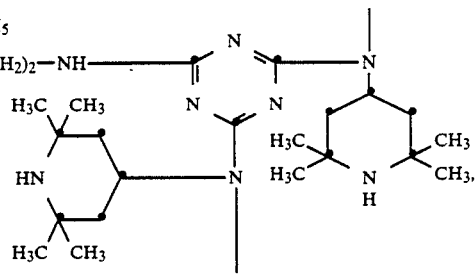
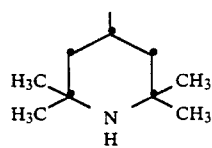
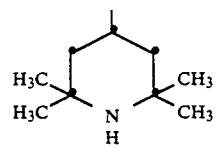
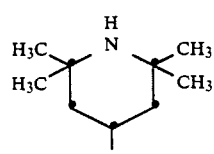

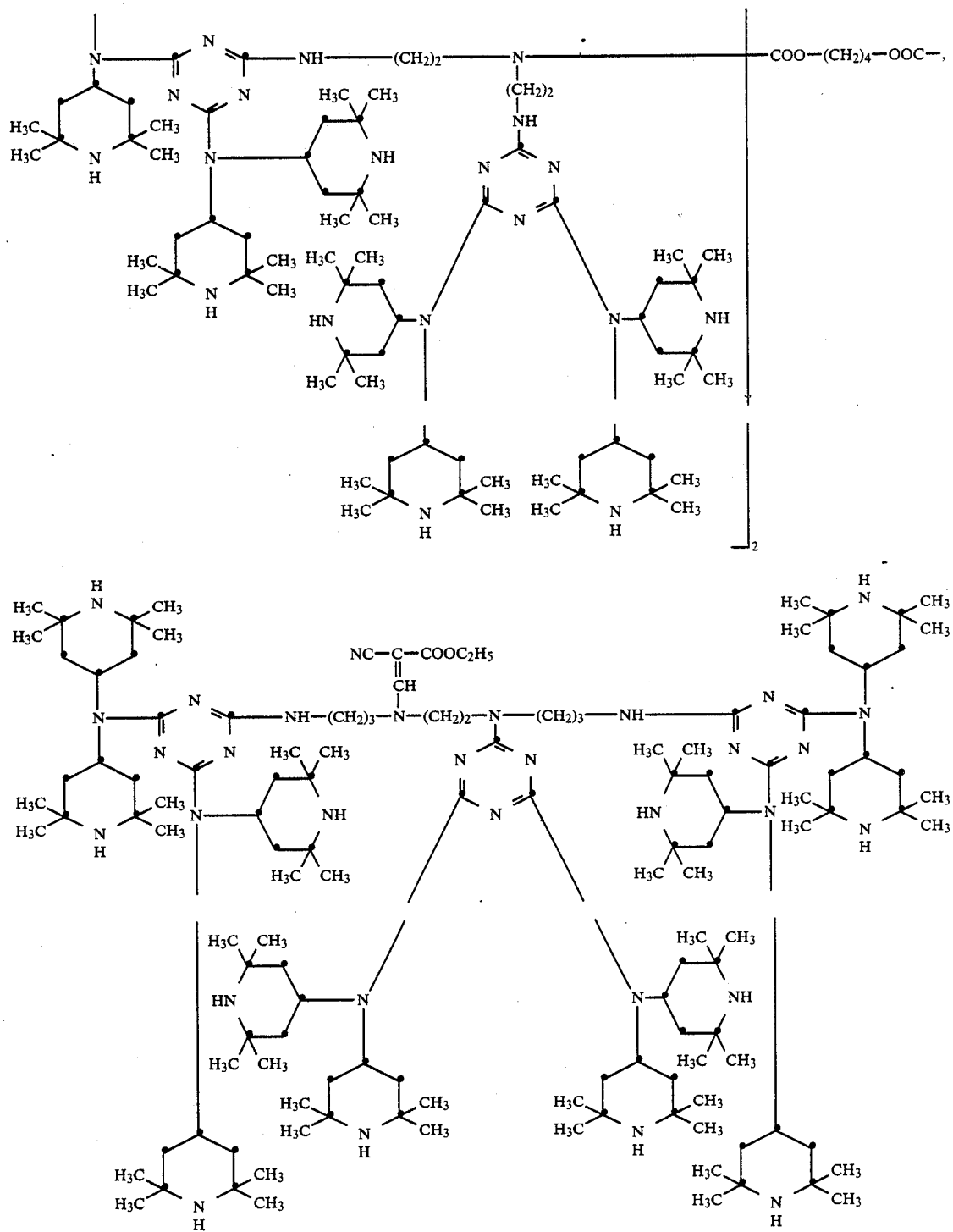
according to claim 1.